(12) United States Patent
Haider

(10) Patent No.: US 7,917,542 B2
(45) Date of Patent: Mar. 29, 2011

(54) SYSTEM AND METHOD FOR MINIMIZING TRANSMITTED DATA BETWEEN DIVERSE INSTITUTIONS

(75) Inventor: Sultan Haider, Erlangen (DE)

(73) Assignee: Siemens Aktiengesellschaft (DE)

( * ) Notice: Subject to any disclaimer, the term of this patent is extended or adjusted under 35 U.S.C. 154(b) by 391 days.

(21) Appl. No.: 12/074,493

(22) Filed: Mar. 4, 2008

(65) Prior Publication Data
US 2009/0228444 A1    Sep. 10, 2009

(51) Int. Cl.
G06F 17/30    (2006.01)
G06F 21/00    (2006.01)

(52) U.S. Cl. .......................................... 707/802; 705/51
(58) Field of Classification Search .................. None
See application file for complete search history.

(56) References Cited

U.S. PATENT DOCUMENTS

| | | | |
|---|---|---|---|
| 6,732,331 B1 * | 5/2004 | Alexander | 715/234 |
| 7,069,227 B1 * | 6/2006 | Lintel et al. | 705/4 |
| 7,426,513 B2 * | 9/2008 | Gvily | 1/1 |
| 2002/0103827 A1 * | 8/2002 | Sesek | 707/505 |
| 2006/0206464 A1 * | 9/2006 | Marukawa | 707/3 |
| 2006/0230033 A1 * | 10/2006 | Halevy et al. | 707/3 |
| 2009/0080408 A1 * | 3/2009 | Natoli et al. | 370/351 |

OTHER PUBLICATIONS

Carol Chou, "Action Plan Background: PDF 1.6", May 20, 2005.*

* cited by examiner

*Primary Examiner* — Neveen Abel-Jalil
*Assistant Examiner* — Tarek Chbouki
(74) *Attorney, Agent, or Firm* — Brinks Hofer Gilson & Lione

(57) ABSTRACT

A system and method transmitting data in heterogeneous networks is described. A plurality of fillable forms is available to a user, each form having a name and metadata corresponding to the data fields that are displayable or retrievable by the form. The same form name is associated with the same metadata at another site, which may be another user or a central data base. When data values are filled in a form, the data values and the form name is transmitted over a network interface. At another location, the data values are received over a network interface, and a form having the same name as that of the received data is retrieved from a forms data base at the receiving location and used either to display the received data values in a form substantially the same as the transmitting form, or to formulate a query to a data base.

10 Claims, 6 Drawing Sheets

(A)

(B)

SYSTEM AND METHOD FOR MINIMIZING TRANSMITTED DATA BETWEEN DIVERSE INSTITUTIONS

TECHNICAL FIELD

The present application relates to a system and method of improving efficiency of medical treatment of patients by optimizing the transmission, storage, and display of medical information.

BACKGROUND

Medical data, stored in electronic data bases comprises a large and heterogeneous category of information on individual patients, and is useful for managing treatment of individuals, administering healthcare and insurance systems, and medical research. Access to such data is ordinarily restricted by law or regulation.

The characteristics, format, and method of storage of such data differs amongst institutions, geographical areas, health care plans, countries, and the like, to the extent that few aspects of the data storage are fully standardized. That is not to say that efforts are not being made to achieve such standardization of format, for example in the DICOM (digital communications in medicine) standard, or others, however many records in physicians offices are still kept in paper format, or in legacy formats that are not interoperable with the presently available digital data formats used by hospitals, for example. Thus, the capability for the entry and retrieval of data regarding patient medical history, test results, existing medications, care plans, and the like, is limited. Some data is not accessible, and others may require the use of specific forms which may not be generally distributed.

From an evolutionary viewpoint, the types and formats of data that may be stored may change with time as the state of medical knowledge advances. New types of data, for example from different imaging modalities, or other diagnostic tests may be obtained for existing patients. Newly discovered relationships between various test results and syndromes may be identified as suitable for diagnostic purposes, and update treatment protocols may require access to data from differing time frames or differing data bases.

Generally, data bases are in a form known as relational data bases, and at present the most common data base query and maintenance language is SQL, or a variant thereof. When data is being transmitted over a telecommunications network, such as the Internet, data may be represented in XML (extensible markup language), which provides structuring and formatting for data which may be displayed on a web page. The data used to format and display information on a web browser page is HTML. For predetermined forms used for data entry and management, the PDF format (portable document format) may be used.

Particularly when retrieving data from a remote data base, the lack of particularity in the formatted request may result in data being retrieved from the data base and transmitted which is substantially in excess of that actually needed by the user. This may also include the data needed to reconstruct the form. While the transmission capacity of data links continues to increase, so do the demands for transmission and, inevitably, at some point in a data network, a bottleneck develops.

SUMMARY

A system for managing patient information is disclosed, including, a central data base having a data base server communicating with a first network interface; a display terminal and a client server communicating with a second network interface; and, a forms data base at the data base server and a forms data base at the client server. The client forms data base may be a subset of the data base server forms data base, and each form may have a unique name and metadata associated with each unique name.

Information filled in fields of a named form at the display terminal may be transmitted through the second interface, the information including a form name of the unique name. The information may be received thought the first network interface and the unique form name used to retrieve metadata from the data base server forms data base, and to formulate a query to the central data base.

A computer program product is described, the product being stored or distributed on a machine readable medium, and having instructions executable by a computer to communicate with a central data base having a data base server communicating over a network with a display terminal and a client server; and, to manage a forms data base at the data base server and a forms data base at the client server. The client forms data base may be a subset of the data base server forms data base; and each form may have a unique name and metadata associated with each unique name.

Information filled in fields of a named form at the display terminal may be transmitted over the network, the information including a form name of the unique names. The unique form name may be used to retrieve metadata from the data base server forms data base and to formulate a query to the central data base.

In another aspect, a method of managing patient information includes providing a locally located forms data base, where each form in the data base may have a name and associated metadata; and, providing a remotely located forms data base. Each form in the data base may have a name and associated metadata. A fillable form may be displayed, the form having a name of the names in the local forms data base. Information may be entered into at least one field of the fillable form, where the information may be a value the fillable field. The information entered into the form, and at least the name of the form, may be transmitted over an interface to a network.

DETAILED DESCRIPTION

Figure 1:
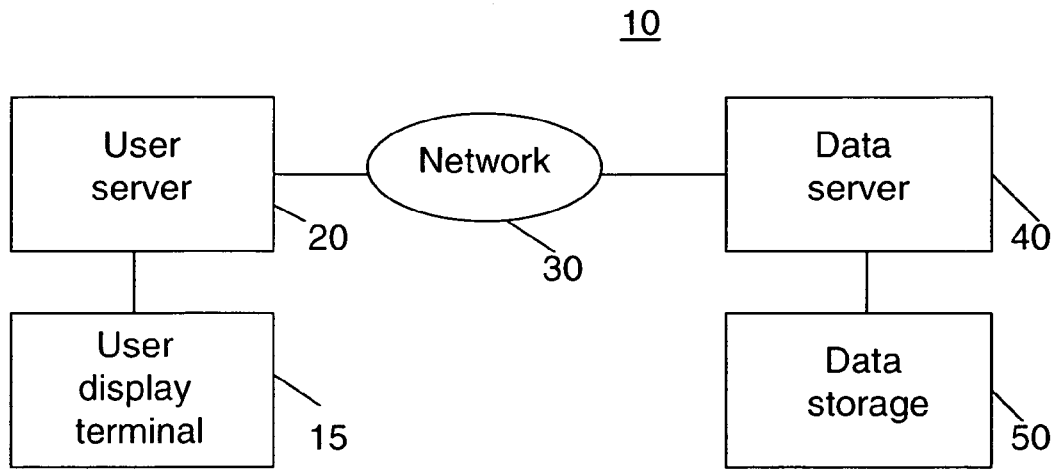
FIG. 1 is a block diagram of a system for using forms to optimize data transmission.

Exemplary embodiments may be better understood with reference to the drawings. Like numbered elements in the same or different drawings perform equivalent functions.

In the interest of clarity, not all the routine features of the examples herein are described. It will of course be appreciated that in the development of any such actual implementation, numerous implementation-specific decisions must be made to achieve a developers' specific goals, such as consideration of system and business related constraints, and that these goals will vary from one implementation to another.

In describing the system and method, recourse is had to the identification of specific data formats, programming constructs and the like which are in current use. The field of telecommunications, computing and data processing is continually evolving, and new or modified standards are being developed and adopted. The use of existing terminology such as HTML, XML, PDF, TCP/IP, and the like may therefore be understood as a convenience in explaining the concepts herein to a person of skill in the current art. Generally, the standards are now evolving so that existing standardized data structures will have conversion software produced so as to be converted into, or to be compatible with evolving standards. The individual software components or programs that may be used to perform the functions and operations described herein may be produced as proprietary software, however such software is at least represented by the suppliers as being compatible with a specific named standard. Nothing herein, however, is intended to preclude the use of non-standardized data formats or the like on a local basis, or the storage of data, which may be images, text, tables, and the like in whichever format is considered appropriate by the organization maintaining the data base in which it is stored.

It should be understood that the extensiveness of the now-existing language structures may permit the same objective to be obtained by differing uses of the various data structures, computational features, or the like. Generally, the user is not concerned with the underlying design of the software or hardware, and the examples given herein are general in nature, as it may be expected that due to the evolutionary nature of large data networks, that the software and hardware available will be heterogeneous. The underlying design objective is to achieve the desired functionality and response times by interoperability between the system components, even if this requires translation from one data format to another, or the like.

It may be convenient to present a user with a set of standardized forms for the purposes of entering or retrieving data from a local or distributed data base. An example of such a form is a fillable PDF form. Such a form, which may have a name, such as "patient data" may be used to enter data regarding a particular patient, and to display data of a particular patient that has been retrieved from a data base. For example, an identification number (which may be a national insurance number, social security number or other unique identification number) may be entered.

The form for the initial request may be the form on which the requested data is presented once it has been retrieved from the data base. Alternatively, additional forms that are specialized to the particular medical service may be invoked by the returned data. These forms may be multipage, and multilevel. In an aspect, where image data is being retrieved, the images may initially be represented by icons or thumbnails, and the user may then navigate through the data set by graphical user interface (GUI) techniques such as point and click, dragging, and the like.

Since PDF files can be byte served over a data network, rapid initial access to large amounts of data may be facilitated. This process is similar to the process of streaming video files where one does not have to download the full file before viewing. After loading and displaying the first part of data, for example, a page, a page-on-demand process continues to download the rest of the file. Thus a user could read the information of the first page and then jump to a page without having to wait.

Arbitrary media types can be embedded in PDF file. Embedded media, as well as referenced media outside a PDF file, can be played with a variety of player software. The term playing can be used with a wide variety of media, and is not restricted to audio or video. For example, it may be applied to static images such as JPEGs. Media objects may have multiple renditions, such as icons, thumbnails, screen resolutions and the like, which can be chosen at play-time, or at the time of formatting for transmission over a network, based on considerations such as available bandwidth.

A combination of HTML and PDF format may enable a system to serve content to the user in its most useful format based on the demands of content versus technology. The data entered in, or displayed on, the form may be described in XFDF which may define a data "container" for annotations (that is to say, for example, data values entered in a PDF form) that is separate from the PDF form to which they apply. The form annotation content could be extracted and transformed into another format, such as a plain text file. Or, the annotations can be modified and imported back to the corresponding PDF document.

XFDF, on the other hand, represents an entry with an XML element/content or attribute/value pair, as shown in the XFDF fragment shown below. In an aspect, the XFDF associated with a particular PDF forms may be considered as part of the document metadata, and be used to identify the format and name of each data field.

```
<field>
    <field name="Street">
        <value>401 N. Michigan Ave.</value>
    </field>
```

In an aspect, the XFDF field names associated with a particular uniquely-named PDF forms document may be considered as part of the document metadata, and be used to identify the format and name of each data field. XFDF conforms to the XML standard, which has gained wide acceptance and is supported by many existing XML tools. For example, XML tools supporting XML Stylesheets (XSLT) can be used to transform an XFDF file to another format (XLST). An XML-based document can be transformed into a different format, such as HTML, CSV, PDF, and Excel.

An XFDF file with form data contains form field names and values. When importing XFDF into a PDF document, the target PDF document already contains the form fields for the data to be imported. Importing XFDF updates the form field values in the PDF file. Conversely, exporting to XFDF puts the current value of the field in the value element.

In an aspect, metadata representing the fields available in the document may be used to pre-filter the XFDF file or XML document either at the data center or at the user location.

The combination of hardware and software to accomplish the tasks described herein may be termed a system. The instructions for implementing processes of the system may be provided on computer-readable storage media or memories, such as a cache, buffer, RAM, removable media, hard drive or other computer readable storage media. Computer readable storage media include various types of volatile and nonvolatile storage media. The functions, acts or tasks illustrated or described herein may be executed in response to one or more sets of instructions stored in or on computer readable storage media. The functions, acts or tasks may be independent of the particular type of instruction set, storage media, processor or processing strategy and may be performed by software, hardware, integrated circuits, firmware, micro code and the like, operating alone or in combination. Some aspects of the functions, acts, or tasks may be performed by dedicated hardware, or manually by an operator.

The instructions may be stored on a removable media device for reading by local or remote systems. In other embodiments, the instructions may be stored in a remote location for transfer through a computer network, a local or wide area network, by wireless techniques, or over telephone lines. In yet other embodiments, the instructions are stored within a given computer, system, or device.

Communications between the devices, the system, subsystems, and applications may be by the use of either wired or wireless connections. Wireless communication may include, audio, radio, lightwave or other technique not requiring a physical connection between a transmitting device and a corresponding receiving device. While the communication may be described as being from a transmitter to a receiver, this does not exclude the reverse path, and a wireless communications device may include both transmitting and receiving functions. Where the term wireless is used, the intent is to describe an apparatus for converting a data value into a modulation on a carrier signal that may be radiated by and an antenna, and the corresponding apparatus for receiving a signal and demodulating the data from the carrier signal, where the transmitter and the receiver constitute an interoperable set, having a known protocol, which may be one of an industry standard, such as IEEE 802.11b/g.

The communications network may be provided by others as a common carrier, leased or fee-for-service transmission medium, and a variety of communications modalities used in the network, which may be reconfigurable. For local low bandwidth connections DSL, ISDN, or cable modem may be used. For higher bandwidths transmission, fiber networks are known.

In an example, shown in FIG. 1, a distributed system 10 may include a user display terminal 15 in communication with a user (client) server computer 20. The user server computer 20 may have an interface with, and communicate over, a network 30, which may be provided by others, so as to transmit and receive data at a network interface (not shown). At another location, a data server computer 40 may receive data and requests for data over the network 30, and retrieve the data from a data storage device 50, and transmit the retrieved data over the network 30 through a network interface (not shown).

Figure 2:
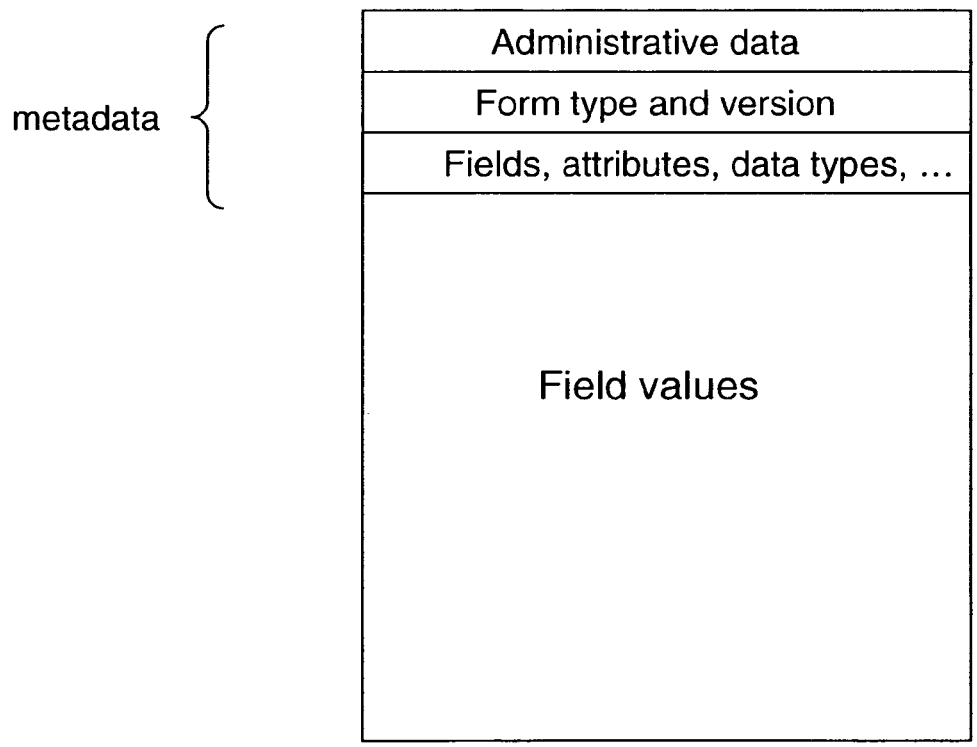
FIG. 2 is a flow chart of the method, where data is being transmitted from one display to another display and the displays have substantially the same form.

In an aspect, shown in FIG. 2, the data may merely be transmitted between two separated terminals and not stored. This example (200) illustrates the basis for reduction of the volume of data which may need to be transmitted between separated display terminals. The data may also be used to update a data base (not shown). A user may fill out a fillable form, which may be a PDF-type form. This form may be a default starting screen, or selected from a menu of forms. As an example, form "A", may be filled out (step 210) with a patient's ID number, address and other such information for an initial registration with the health care network. All of the fillable data areas may be filled with values, or some may be left blank where the information is not available. Check boxes, radio buttons, and the like, may also be provided on the form so as to organize the information. A digital camera may be used to capture a photograph of the patient that is insertable in an image area. Such an image area may, in other forms, be used to enter or retrieve images of the patient such as may be obtained by an imaging modality such as a CT-scanner.

Figure 3:
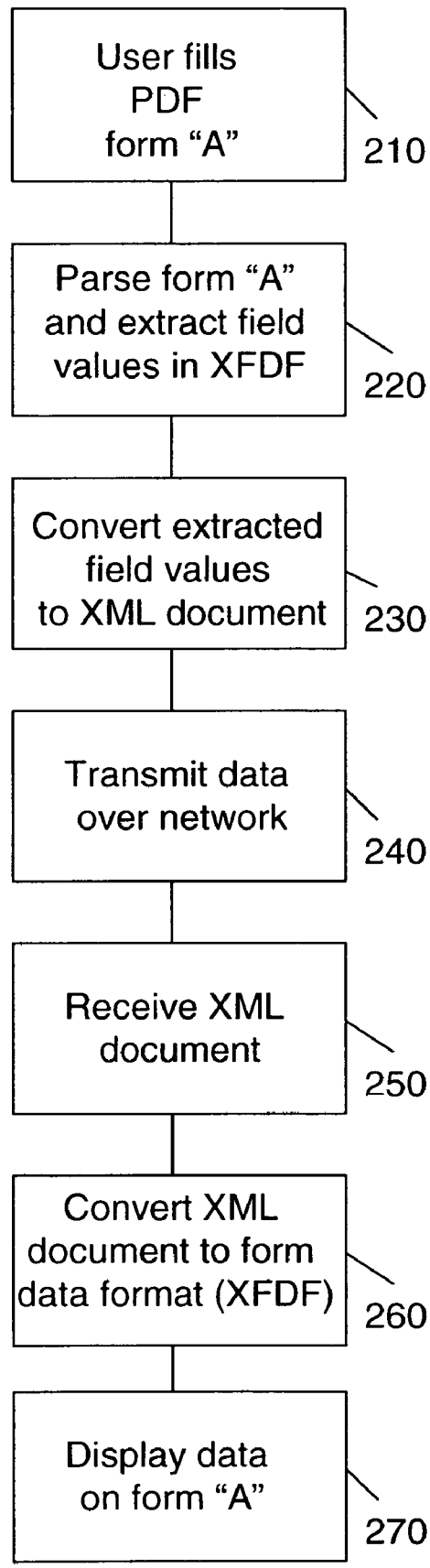
FIG. 3 is a schematic representation of a data structure associated with a form.

When the form "A" has been filled, and edited if necessary, the user actuates a control, which may be a button displayed on the form, so as to transmit the form. This action may cause the document to be parsed and formatted for transmission. Each form may have associated descriptive material, which may be metadata that describes the format and the data elements and types found in the form. An example of such data is shown schematically in FIG. 3. The metadata may include administrative information, including time of generation form, access privileges and the like; a unique form name and the version of the form; a listing of the data elements, names of the data fields, type of data, validity ranges, or the like; and may be followed by the form data (field values), which may be extracted as XFDF data (XML forms data format) (step 220). The extracted data and metadata may be formatted as an XML document or other interoperable format and processed by the user server computer so as to be transmitted over a telecommunications network (step 240). The user server computer may be a personal computer having the forms displayed on the computer display, or a server consolidating the operations of a plurality of users at a site. In some instances, where the two users are determined to be clients of the same server, the step of transmitting the data over the telecommunications network (step 240) may be omitted, and the XML document may be routed to the receiving client directly.

When data is received at another site (step 250), a server computer at that site, in communication with a user, converts the data to XFDF format (step 260) so that it may be loaded into a form for display. In this example, only one form, form "A", is in use, so the form is automatically selected at the receiving site and the data is displayed on form "A". At the receiving display, the form may be edited, and transmitted back to the sending display by repeating the process described, but along a reverse transmission path.

By converting the forms field values (data) into parseable objects, the graphical form has been reduced to a descriptive data stream, which reduces the quantity of data that needs to be transmitted between locations, as only the information content (field values) entered on the form (or retrieved for display on the form) needs to be transmitted. This may be further reduced if the unique name of the form being used points to a storage location where the metadata of the form may be found, and that this file is available at both locations. Then only the form name and field values need to be transmitted.

Figure 4:
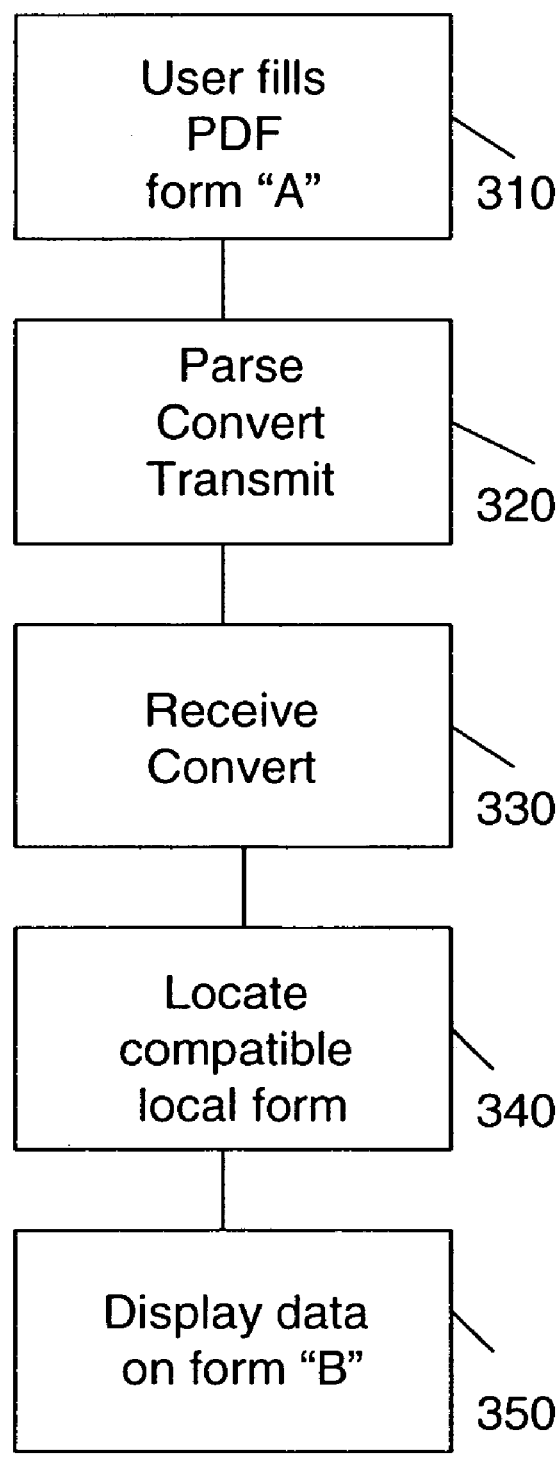
FIG. 4 is a flow chart of the method, where data is being transmitted from one display to another display, where displays use compatible forms.

In another aspect, shown in FIG. 4, a method of transmitting data (500) does not require that the forms on both ends of the communication link have the same attributes. Where multiple forms are possible, the XFDF data are parsed to determine the type of form used to generate the data being processed. If form "A" is available at the site, the data may be displayed on the form. Otherwise, a list of forms is checked for compatibility so that a form that is capable of displaying data, of which the received data is a sub-set, may be chosen. This may accommodate situations where differing institutions have preferences for the form to be used. Such preferences may be only that the forms differ as to the institutional logo that is displayed, or there may be more substantive differences. Depending the function of, for example, the receiving location, data transmitted using form "A" may be displayed on form "B", which might be capable of displaying information regarding insurance coverage, drug interactions or the like, which may separately be retrieved when form "B" is selected.

For example, the user fills information (field values) into form "A" (step 310) and when the form is completed, the form is parsed into XFDF, converted into a XML document and transmitted (step 320). Step 320 may be considered to be the equivalent of steps 220, 230 and 240 in method 200. The data is received at the other site (step 330) and converted into form compatible data. This may be considered to the equivalent of steps 250 and 260 in method 200. At this juncture, the type of form that was used to prepare the data is identified, and a look up is performed at the receiving site so as to identify a compatible form for display, based on the forms available at the receiving site. The form may be the same form "A", or form "B" which is similar to form "A" and may display some or all of the data of form "A", or may also be capable of displaying additional enterable or retrievable data based on the function of the receiving site.

In order to support the evolution of the data management system, new forms and types of data are likely to be needed. The resolution of images may increase, new diagnostics tests may be introduced, and the like, which may render the existing version of a form obsolete. Changes in forms may range from adjusting the format of data fields, to completely new forms. A new form may be designed by a central organization as shown n FIG. 5A; certain aspects of a centrally designed form may be alterable by individual institutions, without affecting the essential characteristics. An updated or new form may be designed and validated (step 610) and when this is done, a corresponding form name and metadata are created, and the metadata may include an XML schema. The form, including the associated metadata, is released for use (step 650).

Figure 5:
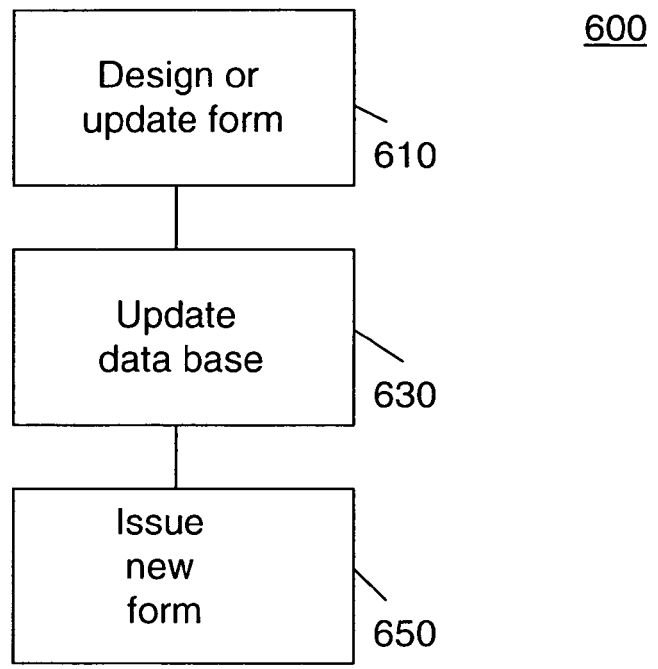
FIG. 5A shows the process of producing forms for use with the system.
FIG. 5B shows the process of distributing forms for use.
Figure 5:
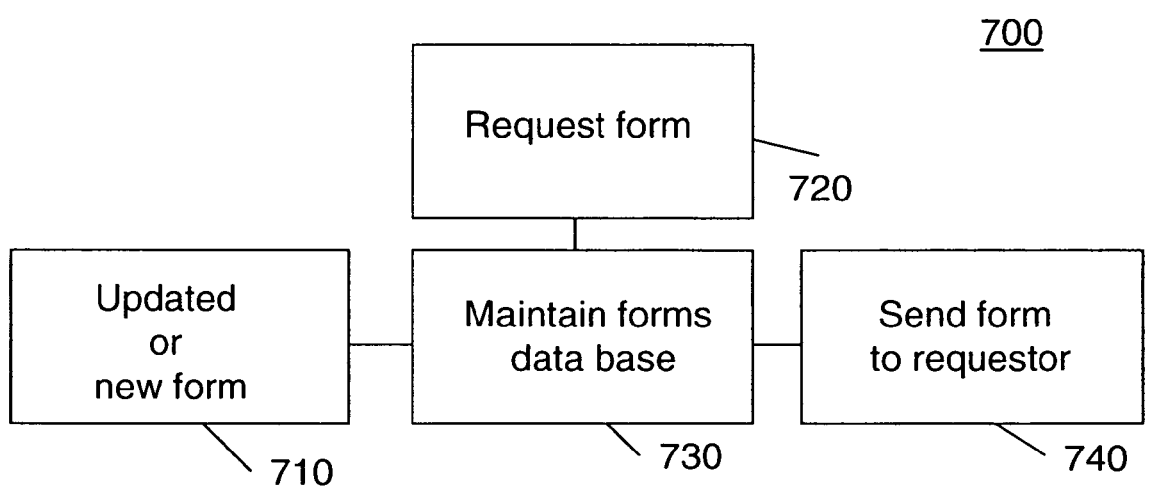

The information on the new form, form "C", is provided to a forms data base (step 710) as shown in FIG. 5B. A data base server may maintain the data base of form attributes (step 730) so that a request for form (step 720) which may be either by form name (e.g. form "C") or by a query using the metadata of the XML document may be satisfied by retrieval of the form descriptor corresponding the a requested form, or a form capable of displaying the data contained in the document may be retrieved and sent to the requester (step 740).

In an aspect, forms released into a central data base may be distributed to local users so as to update a local data base of released named forms. Such named forms may then be rapidly retrieved for filling out or displaying received data. Although a XML document may be transmitted with the expectation that it will be displayed on the same form at the receiving site, the receiving site may substitute a compatible form having more suitable characteristics. The metadata associated with the incoming message, and the originating form name may be used for any returned data.

Thus far, the examples have dealt with the transmission of data from one user to another user, and the editing and return of such data to the originator. However, the data constructs can be used so as to retrieve data from one or more data bases based on the information provided on the filled form. Let us assume that a patient has already been registered with the health system and that some historical data exist for the patient. This data would have been entered into a data base for management and retrieval. Certain of this data may be held in a relational data base, so that it may be retrieved based on specific keys and values. The retrieved data may also be used to point to locations where data is stored in bulk, such as image data files, diagnostic test data, and the like, so that the image, tabular or text data may be retrieved.

A user may be a physician in a particular specially, for example, cardiology. The specialist may wish to determine what relevant diagnostic or patient history data exists for the particular patient. At the institution, the cardiology service may have designed or selected a variety of forms for data retrieval and examination reporting. The available forms may be expressed in a table of form types, or a hierarchical form structure, where the individual types or groups of types of medical data are first represented by icons, which may be selected to prove into the data base. Whether a form displays icons or thumbnails of the data or the full image resolution may depend, for example, on the bandwidth of the telecommunications network connecting the requesting user to the source of data. Therefore, the forms used by differing institutions, for example a local doctor's office or a major hospital, may be similar but display the data in a different hierarchy.

Figure 6:
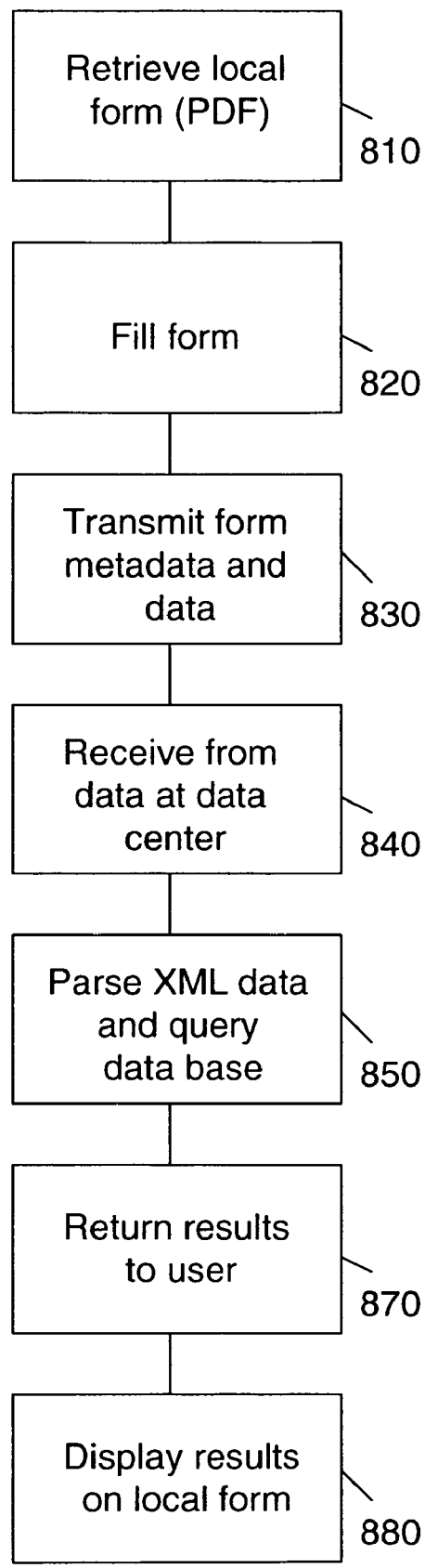
FIG. 6 is a flow chart of the process of using the forms metadata in retrieving data from a data base.

FIG. 6 shows a forms based method of retrieving data from a data base or updating the data base with new medical and administrative data. The method (800) includes the steps of retrieving a local form (step 810) the form being a PDF form having metadata describing the fields of data that may be displayed in the form. For this example, the form has been selected to determine the relevant cardiological history of a specific patient. A user fills out part of the form (step 820) so as to, for example, specify the patient by ID number, and may select specific attributes of the data of interest. These attributes may be a case summary, recent laboratory results, medication history, or the like. The specific design of forms is dependent on the medical specialty, and may be expected to evolve as the best practices are updated based on clinical studies, or other information.

The filled-out form may have a number of unfilled areas, such as details of the patient corresponding to the ID number, however not all fields are required fields, and some of the fields will be filled in by searching the data base. The initial request form may not be the form on which the data is displayed to the user, as the areas for image display may need to be particularized to the image type being retrieved. The data may be returned in a series of hierarchical forms, organized so that the initial response is rapid due to limitation on the types of data initially transmitted, and the backup data being retrieved and transmitted either in a streaming manner, or on demand, when an appropriate icon is selected. When the form has been filled out, the form field data values are extracted (step 830) in a manner that is analogous to steps 220, 230, and 240 previously described. In this instance, the data is transmitted to a data center server, such as data server 40.

The data values provided by parsing the filled-in form, such patient ID, the filled-in areas of the form, and the blank areas of the form are now interpreted by a data base server so as to formulate a data base query. This query may be, for example, a query generated in a commonly used query language such as SQL and interacting with a relational data base (step 850) that is also maintained by the data server 40. Not all of the data that is to be retrieved may be located in the specific data base, and the result of the query (step 860) may be to return pointers to the locations of the desired files. When the data package corresponding to the query has been retrieved, each of the elements of the retrieved data may be parsed to extract metadata related to the data found. Generally this corresponds to a subset of the metadata associated with the data base query, since not all types of data, or all time periods of data, are available in each instance. Since large amounts of data are often displayed on nested forms, the forms to be selected for display of the retrieved data may be selected to correspond to those forms needed to display the data represented by the metadata of the data package. Unneeded forms and links to those forms may not be displayed.

The data values for each field be combined into an XML document, and the data returned to the user (step 870). The user server may parse the metadata to select the corresponding local forms and display the data values in the fields on the forms (step 880).

Figure 7:
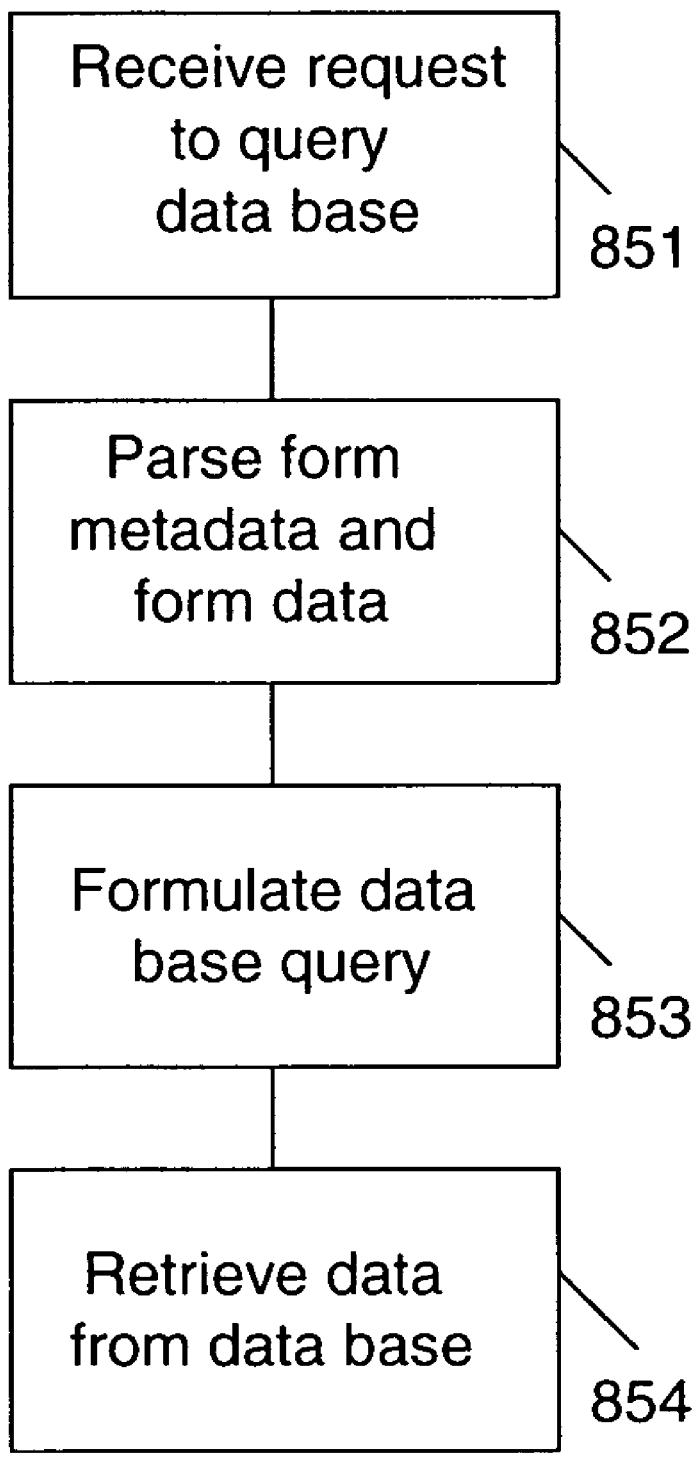
FIG. 7 is a flow chart of the use of the forms metadata in formulating a data base query.

In an aspect, step 850 may be comprised of sub-steps as shown in FIG. 7. The request for information from the data base may be received (step 851) and the metadata and any relevant form data relating to the request may be parsed (step 852), so as to formulate a query to the data program. The data provided by the user as values of fields in filling out the request form is used in conjunction with the metadata associated with the form to provide the information necessary for the data base query (step 853). That is, the information that the forms can display generally constitutes the data to be retrieved (step 854), subject to limitations made by the data actually entered on the form: e.g., the patient ID, the medical specialty, a relevant time period and the like.

The system and method therefore reduces the amount of data that needs to transmitted between users, and between users and a data base, by using forms having a common set of field definitions for the data to be entered or displayed. The metadata associated with the form may be stored both locally and in a remote location, so that using the form name may be sufficient to identify the data fields being transmitted or requested, without transmitting the entire associated metadata. Where the form has particular local formatting, but a common set of fields, the local aspects of the form need not be known to the other locations in the system. Where the data being requested extends beyond the capabilities of a particular form, the metadata associated with the returned data may be used to search a data base of forms, which may be either local or remote, so as to find one or more forms suitable for displaying the data.

Since the forms serve to define the metadata for fields that may be entered or displayed in the form, the updating of forms may be used to provide access to newly added types of fields in the centralized data base.

While the methods disclosed herein have been described and shown with reference to particular steps performed in a particular order, it will be understood that these steps may be combined, sub-divided, or reordered to from an equivalent method without departing from the teachings of the present invention. Accordingly, unless specifically indicated herein, the order and grouping of steps is not a limitation of the present invention.

Although only a few examples of this invention have been described in detail above, those skilled in the art will readily appreciate that many modifications are possible without materially departing from the novel teachings and advantages of the invention. Accordingly, all such modifications are intended to be included within the scope of this invention as defined in the following claims.

What is claimed is:

1. A system for managing patient information, comprising:
a central database having a database server communicating with a first network interface;
a display terminal and a client server communicating with a second network interface;
a forms database at the database server and a forms database at the client server, the client forms database being at least a subset of the database server forms database, each form having a unique name and metadata associated with each unique name;
wherein information filled in fields of a named form at the display terminal is transmitted through the second interface, the information including a form name of the unique names, the information is received through the first network interface and the unique form name used to retrieve metadata from the database server forms database and to formulate a query to the central database; and the named form in each of the client forms database and the database forms database each correspond to a same named form in another forms database.

2. The system of claim 1, wherein the data values extracted from the central database by the query are transmitted through the first network interface and received through the second network interface.

3. The system of claim 2, where the data values received though the second network interface are filled into the form having the form name and displayed.

4. A computer program product, stored or distributed in a tangible form on a computer readable medium, the product comprising:
instructions executable by a computer to:
communicate with a central database having a database server and communicate over a network with a display terminal and a client server;
manage a forms database at the data base server and a forms database at the client server, the client forms database being at least a subset of the database server forms database, each form having a unique name and metadata associated with each unique name;
wherein information filled in fields of a named form of the client server forms data base at the display terminal is transmittable over the network, the information including a form name of the unique names, and the unique form name is used to retrieve metadata from the database server forms data base and to formulate a query to the central database; and the fillable form in the client forms database and a named form in the centrally-located database have the at least the same metadata for filled fields corresponding to the information filled in fields of the named form; and, the named fillable form in each of the client forms database and the database server forms database each correspond to a same named form in another forms database.

5. A method of managing patient information, the method comprising:
providing a locally-located forms database having a plurality of form types, each form type in the locally-located forms database having a unique name and associated form metadata;
displaying a fillable form having a name of the unique names in the locally-located forms database;
entering information into at least one field of the fillable form, the information being at least a value of data inserted into of one of the fillable fields;
transmitting the information entered into the fillable form and at least the unique form name of the fillable form over an interface to a network, except that the metadata associated with the unique form name is not transmitted,
wherein the named tillable form in the locally-located forms database and a named form in a remotely-located database have the same metadata for tillable fields and, the named tillable form in each of the locally-locate forms database and the remotely-located forms database correspond to a same named tillable form in a centrally-located database.

6. The method of claim 5, further comprising:
receiving the transmitted information from the network at a remotely-located location;
retrieving a form from the remotely located forms database using the received form name, or selecting another named form from the remotely-located database having metadata corresponding to the received data;

filling the fields of the retrieved or selected form with the received data values; and displaying the filled form.

7. The method of claim 5, wherein the transmitted data values are formatted as an XML (extensible markup language) document.

8. The method of claim 7, wherein the metadata associated with the fillable form fields have an XFDF (XML forms data format) data structure.

9. The method of claim 5, further comprising:

receiving the transmitted information including the form name over a network interface at a remote location;

retrieving metadata from the remotely located database using the name of the received form;

using the received information and the metadata to formulate a database query for a database located at the remote location;

retrieving data values from the database corresponding to the query;

transmitting the retrieved data values over the network interface.

10. The method of claim 9, further comprising:

receiving the retrieved data values and the form name over the network interface;

selecting the form having the received form name;

filling the received retrieved data values into fields of the selected form; and displaying the filled form.

* * * * *

UNITED STATES PATENT AND TRADEMARK OFFICE
CERTIFICATE OF CORRECTION

PATENT NO. : 7,917,542 B2
APPLICATION NO. : 12/074493
DATED : March 29, 2011
INVENTOR(S) : Sultan Haider It is certified that error appears in the above-identified patent and that said Letters Patent is hereby corrected as shown below:

In the claims:

Column 10, claim 5, line 56, please replace "tillable" with "fillable."

Column 10, claim 5, line 58, please replace "tillable" with "fillable."

Column 10, claim 5, line 59, please replace "tillable" with "fillable."

Column 10, claim 5, line 61, please replace "tillable" with "fillable."

Signed and Sealed this
Twenty-sixth Day of February, 2013

Teresa Stanek Rea
*Acting Director of the United States Patent and Trademark Office*